(12) United States Patent
Seki et al.

(10) Patent No.: US 8,058,072 B2
(45) Date of Patent: Nov. 15, 2011

(54) MICROANALYSIS MEASURING APPARATUS AND MICROANALYSIS MEASURING METHOD USING THE SAME

(75) Inventors: Minoru Seki, Tokyo (JP); Junya Takagi, Yokkaichi (JP); Kazuki Yamamoto, Kyoto (JP); Yoshinori Akagi, Osaka (JP)

(73) Assignee: Sekisui Chemical Co., Ltd., Osaka (JP)

( * ) Notice: Subject to any disclaimer, the term of this patent is extended or adjusted under 35 U.S.C. 154(b) by 229 days.

(21) Appl. No.: 12/445,942

(22) PCT Filed: Oct. 18, 2007

(86) PCT No.: PCT/JP2007/070365
§ 371 (c)(1),
(2), (4) Date: Apr. 17, 2009

(87) PCT Pub. No.: WO2008/047875
PCT Pub. Date: Apr. 24, 2008

(65) Prior Publication Data
US 2010/0317538 A1   Dec. 16, 2010

(30) Foreign Application Priority Data
Oct. 19, 2006 (JP) .................................. 2006-284566

(51) Int. Cl.
*C40B 30/04* (2006.01)
*C40B 40/00* (2006.01)
*C40B 30/10* (2006.01)
*C40B 30/00* (2006.01)

(52) U.S. Cl. ............. 436/43; 422/50; 422/63; 422/68.1; 506/13; 506/12; 506/9; 506/2

(58) Field of Classification Search .................... 436/43; 506/2, 9, 12, 13; 422/50, 63, 68.1
See application file for complete search history.

(56) References Cited

U.S. PATENT DOCUMENTS
5,846,396 A   12/1998 Zanzucchi et al.
(Continued)

FOREIGN PATENT DOCUMENTS
JP   2004-501342 A   1/2004
(Continued)

OTHER PUBLICATIONS

International Search Report for the Application No. PCT/JP2007/070365 mailed Jan. 15, 2008.
(Continued)

*Primary Examiner* — Christine T Mui
(74) *Attorney, Agent, or Firm* — Cheng Law Group, PLLC (57) ABSTRACT

This invention provides a measuring apparatus for microanalysis, which can be simply manufactured and can realize a number of analyses and measurements in a small analyte amount and particularly can analyze and measure a number of analytes having different concentrations and different analytes in a simultaneous and easy manner, and a measurement method of microanalysis using the apparatus. The measuring apparatus for microanalysis is characterized by comprising detection parts of m lines and n rows in communication with a micropassage for a waste solution, chambers of m lines and n rows in communication with the respective detection parts through a mixing flow passage, n first micropassages in communication with the respective line chambers through a passive valve, m second micropassages in communication with respective row chambers through a passive valve, and third micropassages in communication with the respective chambers for supplying gas and/or a washing solution.

14 Claims, 8 Drawing Sheets

U.S. PATENT DOCUMENTS

| | | |
|---|---|---|
| 6,117,396 A | 9/2000 | Demers |
| 6,488,896 B2 | 12/2002 | Weigl et al. |
| 6,717,136 B2 | 4/2004 | Andersson et al. |
| 6,812,457 B2 | 11/2004 | Andersson et al. |
| 7,148,476 B2 | 12/2006 | Andersson et al. |
| 2001/0046453 A1 | 11/2001 | Weigl et al. |
| 2002/0142481 A1 | 10/2002 | Andersson et al. |
| 2004/0016879 A1 | 1/2004 | Andersson et al. |
| 2004/0109793 A1* | 6/2004 | McNeely et al. ............ 422/100 |
| 2004/0120856 A1 | 6/2004 | Andersson et al. |
| 2004/0209381 A1 | 10/2004 | Peters et al. |
| 2004/0239234 A1 | 12/2004 | Andersson et al. |
| 2005/0214947 A1* | 9/2005 | Cox ................................ 436/45 |
| 2005/0279925 A1 | 12/2005 | Andersson et al. |
| 2006/0246416 A1 | 11/2006 | Tani et al. |

FOREIGN PATENT DOCUMENTS

| | | |
|---|---|---|
| JP | 2004-529333 A | 9/2004 |
| JP | 2005-46121 A | 2/2005 |
| JP | 2005-134372 A | 5/2005 |
| JP | 2005-140682 A | 6/2005 |
| WO | WO 01/68238 A2 | 9/2001 |
| WO | WO 01/68238 A3 | 9/2001 |
| WO | WO 02/074438 A2 | 9/2002 |
| WO | WO 02/074438 A3 | 9/2002 |

OTHER PUBLICATIONS

Supplementary European Search Report for the Application No, EP 07 83 0099 dated Mar. 7, 2011.

* cited by examiner

MICROANALYSIS MEASURING APPARATUS AND MICROANALYSIS MEASURING METHOD USING THE SAME

TECHNICAL FIELD

This invention relates to measuring apparatus for microanalysis and measurement method of microanalysis using the apparatus, and particularly relates to a measuring apparatus for microanalysis capable of simultaneously making a large number of measurements and a measurement method of microanalysis using the apparatus.

BACKGROUND ART

With recent progress in microfabrication technology in the semiconductor industry, there have been used analytical instruments that use a microchip in which elements necessary for chemical analysis, including channels, reactors and electrodes for sensing, are integrated on a substrate made such as of silicon or glass. Electrophoresis systems using a microchip for DNA analysis or protein analysis have been already developed and are commercially available. An analysis device using such a microchip (a microanalysis system, a μ-Total Analysis System; μ-TAS) realizes integration of chemical analysis experiments, high throughput, resource saving, space saving and low emission. At the moment, various types of microchips are being developed in the world. Concrete examples of various types of microchips being developed include separation microchips mainly for biochemical analysis and also for electrophoresis and chromatography, assay microchips for immunoassay and enzyme analysis, and microchips for synthetic reaction on which polymerase chain reaction (PCR) is performed. These microchips are easily portable. Therefore, it has been expected that the microchips can be used to make an environmental analysis at sampling site or make a high-accuracy clinical test at bed side.

Patent Document 1 discloses the following device as a measuring device using such a microchip. Specifically, the device disclosed in Patent Document 1 is a device for optically measuring a specific binding substance in a fluid sample and includes a reaction part on at least one surface of which immobilized are first specific binding members each of which can form the specific binding substance by binding specifically to a test substance bound to a second specific binding member to which a fluorescent label or a light-scattering label is bound. Furthermore, a transparent base-material layer is laid through a first space layer on one surface of a transparent waveguide having a light-emission end face and a light absorption layer is laid through a second space layer on the other surface thereof. The first and second space layers are mutually communicated layers for loading a fluid sample therethrough. In this case, the refractive index of the waveguide is set larger than that of the fluid sample.

Patent Document 2 discloses the following on-chip bioassay method as a method capable of simultaneously making a plurality of measurements. In this technique, a microfluid chip for cell introduction is fixed to the under surface of a chip having numerous pores made of a substrate through which a plurality of pores arrayed in a grid are passed, whereby a plurality of microchannels for cell introduction are formed between the chip having numerous pores and the microfluid chip for cell introduction. First, suspended cells are loaded through the microchannels into the pores in the chip having numerous pores. Next, a microfluid chip for test substance introduction is fixed to the top surface of the chip having numerous pores to cross its plurality of microchannels for test substance introduction and the plurality of microchannels for cell introduction, whereby a plurality of microchannels for test substance introduction are formed between the chip having numerous pores and the microfluid chip for test substance introduction. Then, a test substance is loaded through the above microchannels into contact with the cells in the pores in the chip having numerous pores, and the degree of influence of the test substance on the cells is detected in situ after a definite time or at definite time intervals.

Patent Document 1: Published Japanese Patent Application No. 2005-140682

Patent Document 2: Published Japanese Patent Application No. 2005-46121

DISCLOSURE OF THE INVENTION

However, in the case of using the optical measuring device described in Patent Document 1, only a single kind of test substance can be measured with a single device but a large number of different test substances cannot be simultaneously measured with a single device.

On the other hand, in the on-chip bioassay method described in Patent Document 2, it is difficult to accurately mix the suspended cells and the test substance based on a desired mixing ratio. In addition, in introducing a sample and a reagent, it is necessary to operate feed pumps and valves connected to the chip. This complicates the work of introducing the sample and the reagent. Therefore, in the case of using the on-chip bioassay method described in Patent Document 2, advanced techniques are required in order to make a quantitative measurement with high repeatability, and it is difficult to provide an easy and stable measurement.

With the above disadvantages in mind, an object of the present invention is to provide a measuring apparatus for microanalysis that can be easily manufactured and can make a large number of analyses and measurements with a small amount of sample and particularly can simultaneously and easily analyze and measure a large number of samples having different concentrations and a large number of different analytes, and a measurement method of microanalysis using the apparatus.

A measuring apparatus for microanalysis according to the present invention is characterized by including: sensing parts in an array of m rows and n columns, each of the sensing parts being communicated with a waste solution microchannel; chambers in an array of m rows and n columns, the chambers being communicated through each mixture channels to the each sensing parts, n first microchannels each communicated through m passive valves with the each m chambers, one chamber per each row of chambers; m second microchannels each communicated through n passive valves with the respective n chambers, one chamber per each column of chambers; and a third microchannel, communicated with the chambers, for supplying gas and/or washing solution to the chambers.

In the sensing parts, measurement is made by any one of appropriate measuring methods, including optical measuring methods and electrochemical analysis. The m×n sensing parts are arranged in an array of m rows and n columns at vertically and horizontally regular intervals, where m and n are positive integers. If m and n are too small, the number of possible simultaneous analyses and measurements is small. On the other hand, if m and n are too large, there arise a problem that the size of this apparatus is increased and a problem that the manufacture of this apparatus is difficult. Therefore, each of m and n is preferably 2 to 10 and more preferably 3 to 6. The chambers and the mixture channels are both arranged in an array of m rows and n columns at vertically and horizontally regular intervals. In other words, each of the number of chambers disposed and the number of mixture channels disposed is m×n in total.

The number of first microchannels disposed in the apparatus is n and each of them is communicated with the associated column of chambers through the respective passive valves. Therefore, solution fed through one end of each first microchannel is weighed out a fixed amount in the associated passive valve and the solution weighed out is fed to the associated chamber. The n first microchannels are preferably separated from each other. Thus, n kinds of solution having different concentrations or containing different ingredients can be fed to the sensing parts.

The number of second microchannels disposed in the apparatus is m and each of them is communicated with the associated row of chambers through the respective passive valves. Therefore, solution fed through one end of each second microchannel is weighed out a fixed amount in the associated passive valve and the solution weighed out is fed to the associated chamber. The m second microchannels are preferably separated from each other. Thus, m kinds of solution having different concentrations or containing different ingredients can be fed.

The first microchannels and the second microchannels are configured to distribute solution, such as a sample or a reagent, through the passive valves to the plurality of chambers arrayed in a matrix, thereby feeding to each chamber a fixed amount of sample or reagent. Therefore, the upstream ends of the first microchannels and the upstream ends of the second microchannels are preferably connected to respective gas supply sources, such as gas pumps. Each gas supply source may be connected directly to the associated microchannel or may be connected through a sample reservoir or a reagent reservoir to the associated microchannel.

Each chamber is connected through the associated mixture channel to the associated sensing part. Solution weighed out in the first microchannels and solution weighed out in the second microchannels are fed to the chambers and then fed to the sensing parts while being mixed together in the mixture channels. The shape of each mixture channel is sufficient if it is a shape allowing solution weighed out in the associated first microchannel to be mixed with solution weight out in the associated second microchannel. Examples of such a shape include a shape that the channel bents and turns back. The mixture channel may be partly widely expanded. Furthermore, the mixture channel may have a laterally asymmetric wall surface.

The third microchannel is connected to the upstream side of each chamber located opposite to the end thereof communicated with the mixture channel. The third microchannel is configured to supply gas and/or washing solution to the chambers in order to feed the solution fed to the chambers to the sensing parts and/or to clean the chambers and the sensing parts and, therefore, preferably connected at the upstream end thereof to a washing solution reservoir and/or a gas supply source, such as a gas pump, in order to supply the gas and/or the washing solution.

Each sensing part is connected to a waste solution microchannel. The other end of the waste solution microchannel is in communication with the atmosphere. In feeding the solution, the air in the system is exhausted through the other end of the waste solution microchannel and unnecessary waste solution can be also exhausted through the other end thereof. Note that "connected with the atmosphere" includes connection to a large-capacity container and connection to a container having a gas diffuse transmission film.

The measuring apparatus for microanalysis is an apparatus assembled such as into a microchip to make an analysis and a measurement with a small amount of sample. Therefore, the volume of each chamber and the volume of each sensing part are preferably of the order of picoliters to microliters. Furthermore, for the purposes of accurate analysis and measurement, it is desirable to fully fill the sensing part with solution fed to the chamber. Therefore, the volume of the chamber is preferably equal to or larger than the volume of the sensing part.

The waste solution microchannel, the sensing parts, the mixture channels, the chambers, the passive valves, the first microchannels, the second microchannels and the third microchannel are preferably formed in a substrate. However, it is difficult to form all these elements in a single substrate. Therefore, they may be formed separately in a plurality of substrates and the plurality of substrates may be then laid one on top of another and bonded to each other. For example, preferably, recesses for the mixture channels, recesses for the chambers, recesses for the first microchannels, recesses for the passive valves each communicated with one of the recesses for the first microchannels and one of the recesses for the chambers and a recess for the third microchannel are formed in one surface of a first substrate, recesses for the second microchannels, recesses for the passive valves each communicated with one of the recesses for the second microchannels and a recess for the waste solution microchannel are formed in one surface of a second substrate, through holes for the sensing parts and through holes for communicating the respective recesses for the chambers with the respective passive valves communicated with the second microchannels are formed in a third substrate, and the sensing parts, the chambers, the passive valves, the first microchannels, the second microchannels, the third microchannel and the waste solution microchannel are formed by laying the third substrate between the one surface of the first substrate and the one surface of the second substrate.

A first microanalysis measuring method according to the present invention is characterized by including: feeding a sample containing an analyte and a reagent containing recognition molecules bindable specifically to the analyte to each of the first microchannels and each of the second microchannels, respectively, in the measuring apparatus for microanalysis according to the present invention; weighing out the analyte and the reagent in the associated passive valves; feeding each pair of analyte and reagent thus weighed out to the associated chamber into a mixed solution, causing mixing and reaction of the mixed solution in the chamber and the associated mixture channel; then feeding the mixed solution to the associated sensing part to bind unreacted recognition molecules in the mixed solution to a standard immobilized to the sensing part; cleaning the sensing part; and then optically measuring the recognition molecules bound to the standard with optical labels providing fluorescence, light scattering or light absorption.

A typical example of the recognition molecule bindable specifically to the analyte is a substance in which a molecule bindable specifically to the analyte is bound to a labeling substance for determination. Labeling substances preferably used are optical labels, enzyme labels or metal labels. The optical labels means labels providing optical effects, such as fluorescence, light scattering, light absorption or chemiluminescence. The optical labels producing fluorescence are particularly referred to as fluorescence labels. The fluorescence labels are substances which when irradiated with light rays, convert the light rays to produce fluorescence. Concrete examples of the fluorescence labels include compounds producing fluorescence when irradiated with light rays, and synthetic resin particles containing such a compound producing fluorescence. In the case of using enzyme labels or metal labels, the same light emission system as in the optical labels can be implemented by introducing through the third microchannel a reagent that can emit light by interaction with the above labels.

Concrete examples of compounds producing fluorescence include fluorein isothiocyanate, fluorescein, fluorescein-N-hydroxysuccinimide ester, 6-((4-(4,4-difluoro-5-2-thienyl)-4-bora-3 a,4a-diaza-5-indacene-3-yl)phenoxy)acetyl)amino) hexanoic acid, succinimidyl ester, 4-acetamide-4'-isocyanatostilbene-2,2'-disulfonic acid, 7-amino-4-methylcoumarin, 7-amino-4-trimethylcoumarin, N-(4-anilino-1-naphthyl)maleimide, dansyl chloride, 4',6-diamidino-2-phenylindole, 5-(4,6-dichlorotriazin-2-yl) aminofluorescein, 4,4'-diisothiocyanatostilbene-2,2'-disulfonic acid, eosin isothiocyanate, erythrosin B, fluorescamine, fluorescein-5(6)-carboxamidocaproic acid N-hydroxy succinimide ester, 5-isothiosyanante diacetate, 4-methylumbelliferone, o-phthaldialdehyde, QFITC, rhodamine B isothiocyanate, sulforhodamine 101 acid chloride, tetramethyl-rhodamine isothiocyanate, 2',7'-difluorofluorescein, cyanine dye, rhodamine and rare earth metal complexes. Among them, rare earth metal complexes with a long luminescence lifetime are particularly preferable.

A light-scattering label is a compound or fine particles which when irradiated with light rays, can scatter the light rays. Concrete examples of such a light-scattering label include aggregates of colloidal fine particles of metal, such as gold or silver, chalcogenide fine particles, such as CdS or CdSe, polymer fine particles, such as polystyrene resin, polycarbonate resin or poly(metha)acrylic resin, inorganic oxide fine particles, such as silica gel, alumina or titanium oxide, and core shell fine particles of a combination of two or more of these materials. The polymer fine particles and inorganic oxide fine particles may be dyed or may be dispersed with fluorescent molecules or metal nanoparticles. The light-scattering label may have a light-scattering characteristic with a wavelength dependence.

The molecules bindable specifically to the analyte are those that can bind specifically to a test substance.

Therefore, the kind of molecules bindable specifically to the analyte differs from analyte to analyte and from standard to standard. Concrete examples of such molecules include a material selected from the group consisting of enzymes, microbes, antigens, antibodies, antibody fragments, lectins, receptors, ionophores, proton pumps, biomembranes, artificial biochips, DNA molecules, RNA molecules, PNA molecules, membrane proteins, intranuclear receptors, aptamers, sugars, glycoproteins and metalloproteins and a mixture of any materials selected from the group.

The standard is a substance that behaves like the analyte towards the molecules bindable specifically to the analyte. The standard may be a substance or molecules having exactly the same structure as the analyte or may be a substance or molecules having a structure corresponding to recognition sites of molecules bindable specifically to the analyte. Concrete examples of the standard include enzymes, microbes, antigens, antibodies, antibody fragments, lectins, receptors, ionophores, proton pumps, biomembranes, artificial biochips, DNA molecules, RNA molecules, PNA molecules, proteins, amino acids, sugars, glycoproteins, metalloproteins and metal ions.

Therefore, in immunoassays, an analyte, a standard and an antibody or antigen are used. Used therein as molecules bindable specifically to the analyte is an antigen or antibody reactable specifically to the analyte.

A second microanalysis measuring method according to the present invention is characterized by including: feeding a sample containing an analyte and a reagent containing recognition molecules bindable specifically to the analyte to each of the first microchannels and each of the second microchannels, respectively, in the measuring apparatus for microanalysis according to the present invention; weighing out the analyte and the reagent in the associated passive valves; feeding each pair of analyte and reagent thus weighed out to the associated chamber into a mixed solution, causing mixing and reaction of the mixed solution in the chamber and the associated mixture channel; then feeding the mixed solution to the associated sensing part to bind unreacted recognition molecules in the mixed solution to a standard immobilized to the sensing part; cleaning the sensing part; and then electrochemically measuring the recognition molecules bound to the standard. The recognition molecules may be labeled with a compound or substance having a high electrochemical response.

The second microanalysis measuring method according to the present invention is the same as the previously-described microanalysis measuring method according to the present invention, except that recognition molecules bound to the standard are electrochemically measured. The present invention can employ any well-known electrochemical analysis. Concrete examples of such an electrochemical analysis include voltammetry, stripping voltametry, amperometry, potentiometery and coulometry. Concrete examples of a waveform of voltage or current applied in these electrochemical analysis s include appropriate pulse waveforms, differential pulse waveforms, triangular pulse waveforms and step pulse waveforms.

A third microanalysis measuring method according to the present invention is characterized by including: feeding a sample containing an analyte and a reagent producing a color or emitting light by reaction specific to the analyte, by addition of a third ingredient or spontaneously to each of the first microchannels and each of the second microchannels, respectively, in the measuring apparatus for microanalysis according to the present invention; weighing out the analyte and the reagent in the associated passive valves; feeding each pair of analyte and reagent thus weighed out to the associated chamber into a mixed solution, causing mixing and reaction of the mixed solution in the chamber and the associated mixture channel; and measuring the produced color or the emitted light of the mixed solution in the associated sensing part. If the addition of the third ingredient is needed, the third ingredient can be introduced, for example, through the third microchannel.

Concrete examples of the compound with which the substance reactable specifically to the analyte is modified includes enzymes including peroxidase and alkaline phosphatase. Concrete examples of the reagent producing a color or emitting light by reaction to the analyte include tetramethyl-benzidine, AMPREX RED and luminol.

A fourth microanalysis measuring method according to the present invention is characterized by including: feeding a sample containing an analyte and a reagent containing a substance forming aggregates by reaction specific to the analyte to each of the first microchannels and each of the second microchannels, respectively, in the measuring apparatus for microanalysis according to the present invention; weighing out the analyte and the reagent in the associated passive valves; feeding each pair of analyte and reagent thus weighed out to the associated chamber into a mixed solution, causing mixing and reaction of the mixed solution in the chamber and the associated mixture channel; and measuring the turbidity of the mixed solution in the associated sensing part.

Concrete examples of the compound with which the substance reactable specifically to the analyte is modified includes lipid membrane, gold colloid and latex particles.

A fifth microanalysis measuring method according to the present invention is characterized by including: feeding a sample containing an analyte and a reagent containing recognition molecules bindable specifically to the analyte to each of the first microchannels and each of the second microchannels, respectively, in the measuring apparatus for microanalysis of any one of claims 1 to 7; weighing out the analyte and the reagent in the associated passive valves; feeding each pair of analyte and reagent thus weighed out to the associated chamber into a mixed solution, joining each of analyte recognition molecules of another kind immobilized in the chamber, the analyte and the recognition molecule derived from the reagent in a sandwiched method; then introducing through the third microchannel into the chamber a solution of a substance digestable with a labeling enzyme on the recognition molecule to displace the mixed solution in the chamber; introducing a product obtained by digestion with the labeling enzyme to the associated sensing part and trapping the product in the sensing part; and indirectly determining the analyte concentration in the sample by measuring in the sensing part the concentration of the product trapped in the sensing part.

Specifically, the method may be configured to use thiocholine esterase as the labeling enzyme, thiocholine as the substance digestable with the labeling enzyme and thiol as the product obtained by digestion with the labeling enzyme and contain a precious metal, such as gold or silver, in the sensing parts. In this case, the product obtained by digestion with the labeling enzyme, such as thiol, is trapped in the sensing parts. The thiol on the precious metal film can be determined by surface plasmon absorption measurement or electrochemical measurement.

Alternatively, an alcohol oxidase, a low-molecular-weight alcohol and aldehyde may be used as the labeling enzyme, the substance digestable with the labeling enzyme and the product obtained by digestion with the labeling enzyme, respectively. In this case, aldehyde corresponding to an oxide of the low-molecular-weight alcohol is trapped in the sensing parts. Therefore, the sensing parts may contain modified molecules having alkaline functional groups, such as amine, for trapping low-molecular-weight aldehyde.

EFFECTS OF THE INVENTION

The present invention can provide a microanalysis measuring method that can be simply manufactured and can make a large number of analyses and measurements with a small amount of sample and particularly can simultaneously and easily analyze and measure a large number of samples having different concentrations and a large number of different analytes.

BRIEF DESCRIPTION OF DRAWINGS

FIG. 1 is a plan view of a substrate 1a.
FIG. 4 is a plan view of a substrate 2a.
FIG. 5 is an enlarged plan view showing an essential part of the substrate 2a.

LIST OF REFERENCE CHARACTERS

1 . . . first substrate
1a . . . substrate
1b . . . substrate
2 . . . second substrate
2a . . . substrate
2b . . . substrate
3 . . . third substrate
4 . . . first microchannel
5 . . . second microchannel
6 . . . third microchannel
7 . . . waste solution microchannel
8, 9 . . . passive valve
10 . . . chamber
11 . . . sensing part
12 . . . mixture channel

BEST MODE FOR CARRYING OUT THE INVENTION

First Embodiment

First, a description is given of the principle of a passive valve with reference to the drawings.

Figure 10:
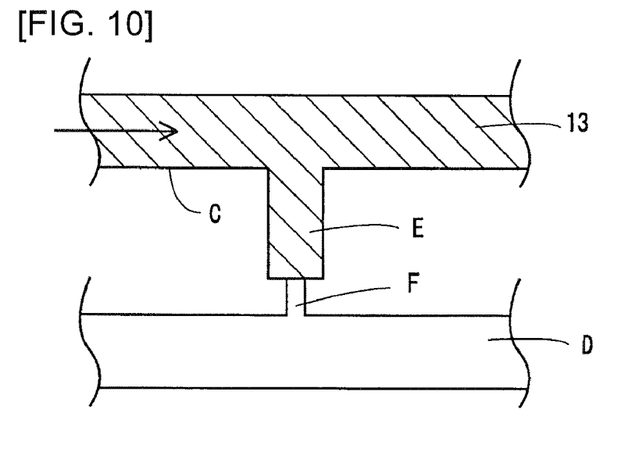
FIG. 10 is a conceptual illustration for explaining the principle of a passive valve.
Figure 11:
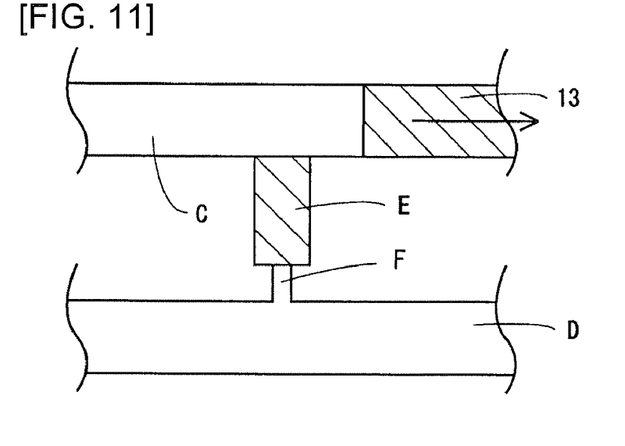
FIG. 11 is another conceptual illustration for explaining the principle of the passive valve.
Figure 12:
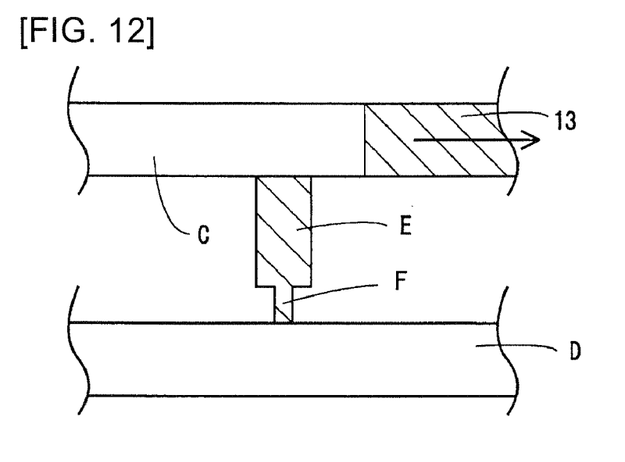
FIG. 12 is still another conceptual illustration for explaining the principle of the passive valve.

FIGS. 10 to 12 are conceptual illustrations for explaining the principle of a passive valve. Channel E and channel F are disposed between channel C and channel D. Channel E is connected to channel C. An end of channel E is connected via channel F to channel D.

As shown in FIG. 10, when a solution 13 is introduced into channel C, the solution 13 is drawn into channel E. If channel E is relatively broad, the solution 13 is drawn into channel E by the pressure of introducing the solution into channel C. If channel E is relatively narrow and has a channel wall easy to wet, the solution 13 is easily drawn into channel E by capillary attraction. On the other hand, if channel E is relatively narrow and has a channel wall hard to wet, the solution 13 can be pressed into channel E by applying an adequate pressure to channel E from the channel C side. Note that the term "channel wall hard to wet" used here can be replaced by the term "channel wall less subject to capillary attraction".

If channel C and channel E have channel walls easy to wet, it is sufficient if channel E is formed to be narrower than channel C. Thus, the solution 13 can be spontaneously drawn from channel C into channel E by a stronger capillary attraction. If channel C and channel E have channel walls hard to wet, the solution 13 can be introduced into channel E by applying an adequate pressure to the solution 13 from the channel C side.

Channel F is narrower than channels C, D and E. Therefore, the solution 13 stops at the inlet interface or the outlet interface of channel F.

Specifically, if channel F has a channel wall hard to wet, the flow of solution 13 having reached the end face of channel F near channel E is, as shown in FIGS. 10 and 11, stemmed by the capillary repulsion of channel F and does not enter channel F. Also if channel E has a channel wall hard to wet, the solution 13 does not enter channel F because the capillary repulsion of channel F is stronger than that of channel E.

On the other hand, if channel F has a channel wall easy to wet, as shown in FIG. 12, the solution 13 having reached the end face of channel F near channel D is drawn into channel F by the capillary attraction of channel F. Note that since channel F is narrower than channel D, the solution 13 stops at the outlet interface of channel F by capillary attraction and does not enter channel D.

If the channel wall of channel F at the outlet thereof and the channel wall of channel D do not make a right angle but form a smooth curved face, the capillary attraction at the outlet of the channel located at the bottom thereof is small, which might leak the solution little by little to channel D. In addition, it is difficult to shape the outlet interface of channel F with a right angle. Therefore, channel F is preferably formed of a channel wall having less wettability.

Note that the term "less wettability" means a property of the channel wall that when solution is drawn into channel C, it cannot pass through the channel with the current pressure and stops in the channel, or generally means that the angle of contact of solution with the channel wall is 90 degrees and up.

After the introduction of the fluid into channel E, the residual solution 13 in channel C is moved to a point in channel C where the solution 13 does not come into contact with channel E, such as by creating an adequate pressure difference between both ends of channel C. Alternatively, the solution 13 may be removed from channel C. In these cases, normally, the solution 13 in channel E does not return to channel C. Therefore, the solution can be weighed out by a volume corresponding to the capacity of channel E or the total capacity of the capacity of channel E and the capacity of channel F.

The solution 13 weighed out in channel E or in channels E and F can be transferred to channel D, such as by creating an adequate pressure difference between channels C and D so that the pressure in channel C becomes slightly larger than that in channel D.

Figure 1:
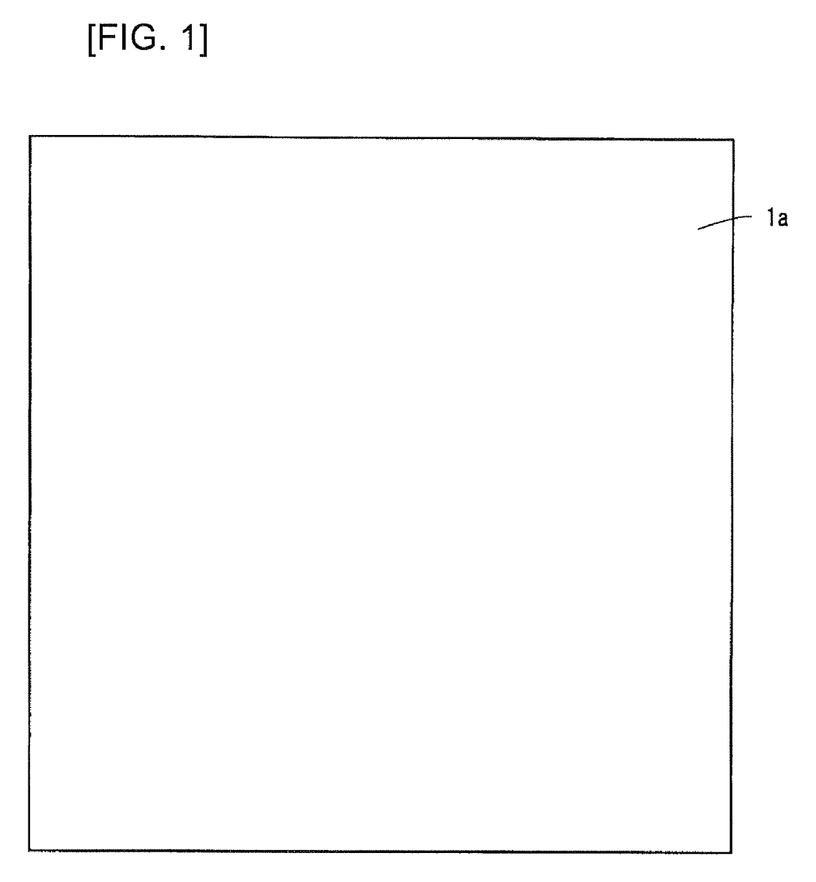
Figure 2:
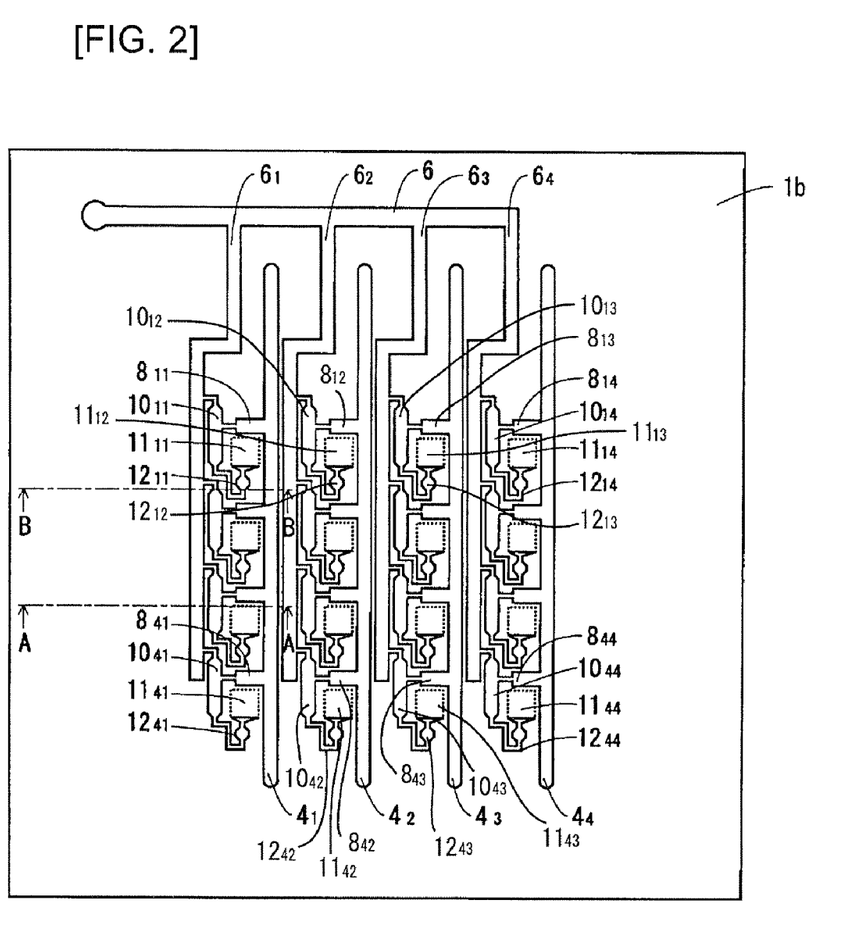
FIG. 2 is a plan view of a substrate 1b.
Figure 3:
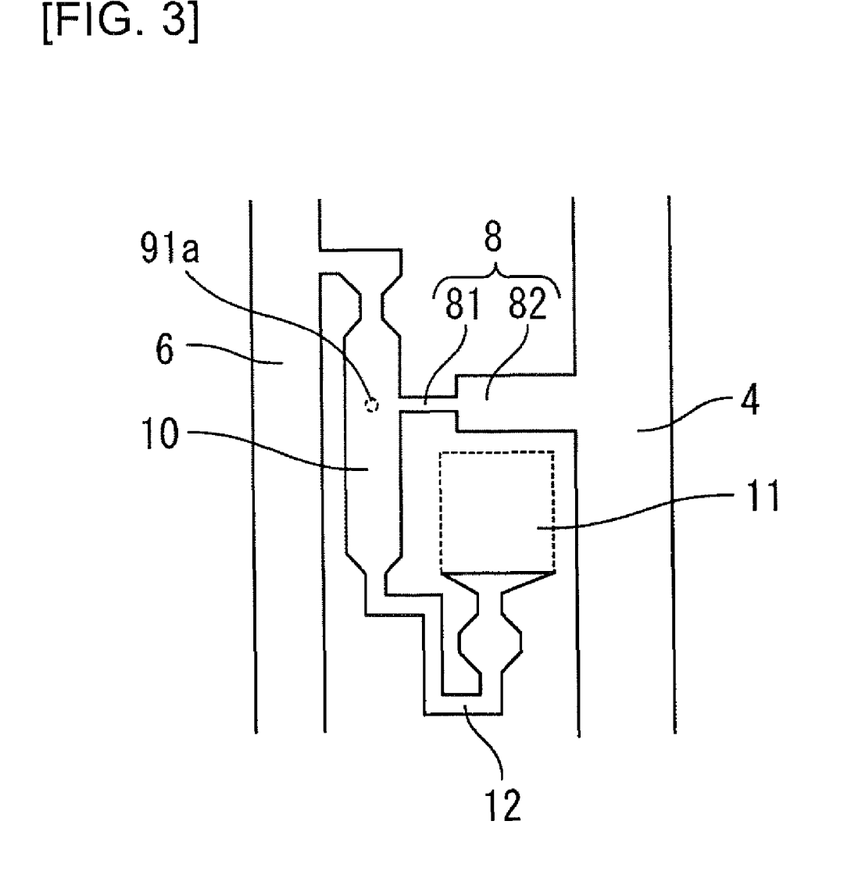
FIG. 3 is an enlarged plan view showing an essential part of the substrate 1b.
Figure 4:
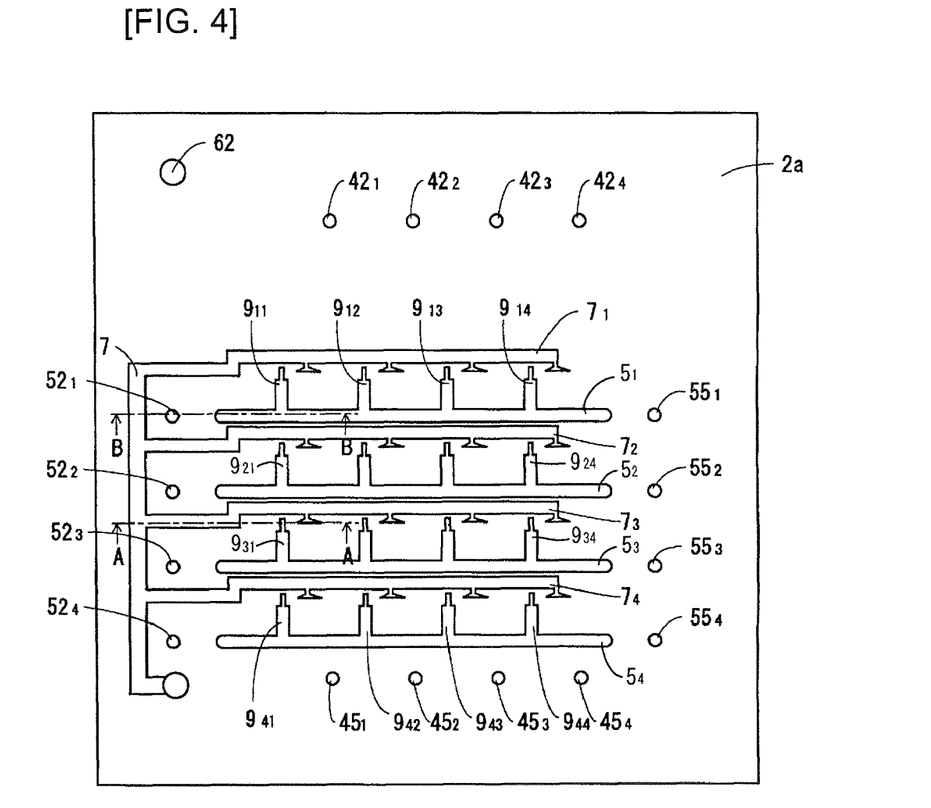
Figure 5:
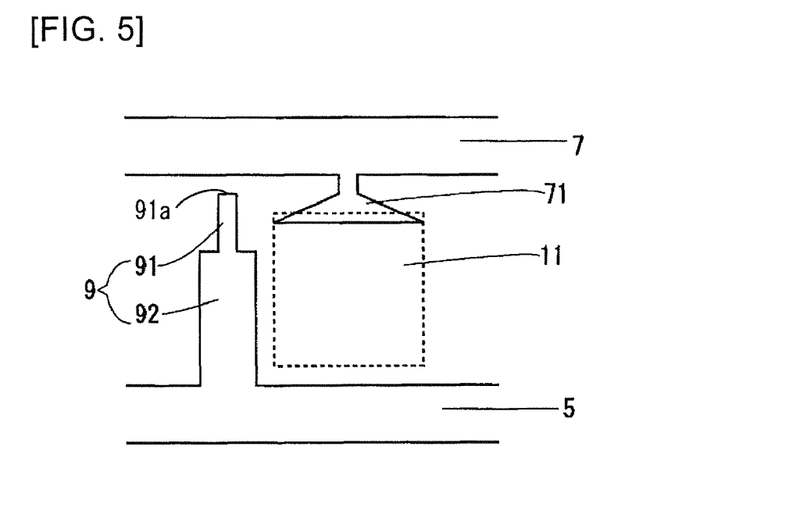
Figure 6:
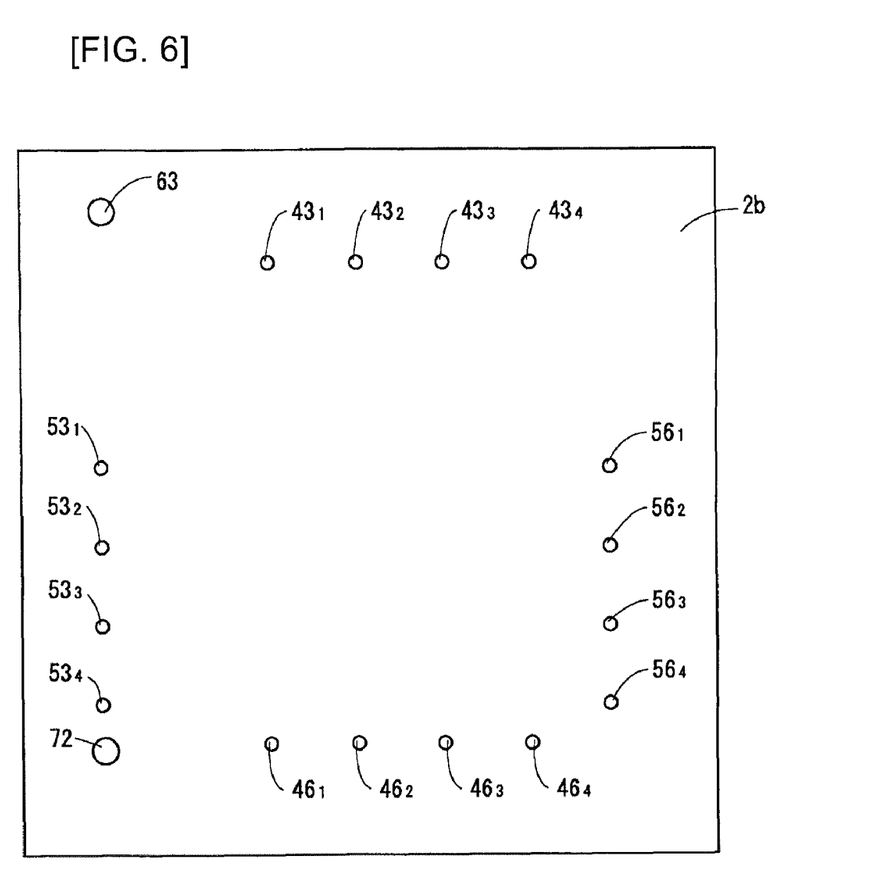
FIG. 6 is a plan view of a substrate 2b.
Figure 7:
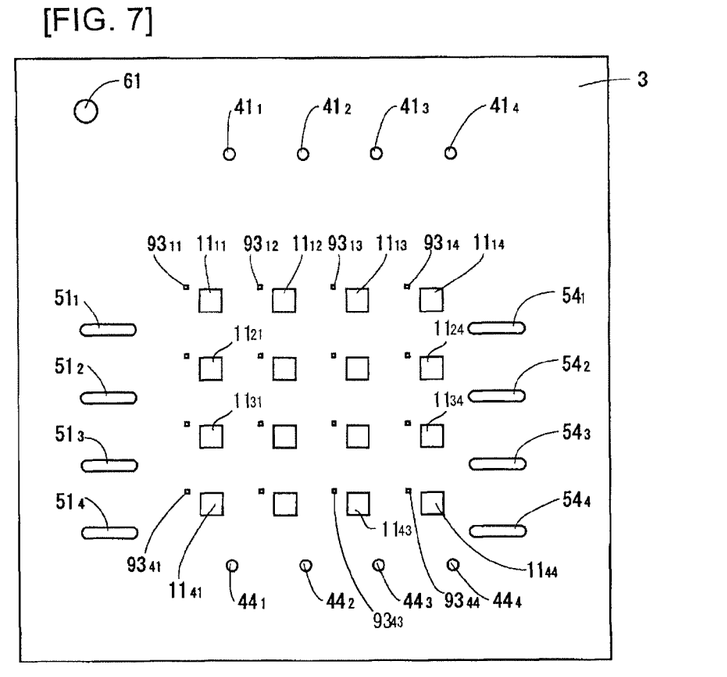
FIG. 7 is a plan view of a third substrate.
Figure 8:
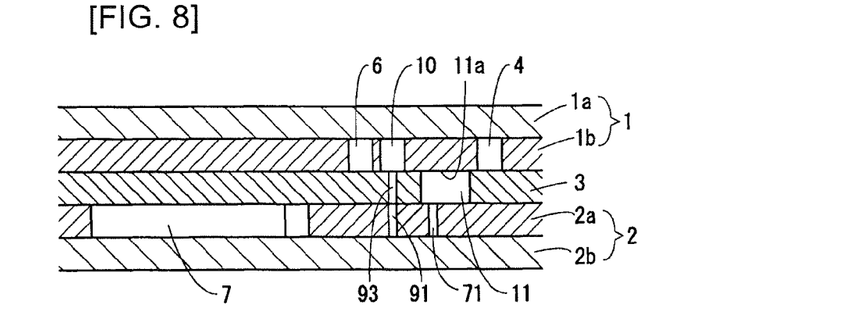
FIG. 8 is a cross-sectional view of a measuring apparatus for microanalysis taken along the line A-A shown in FIG. 2.
Figure 9:
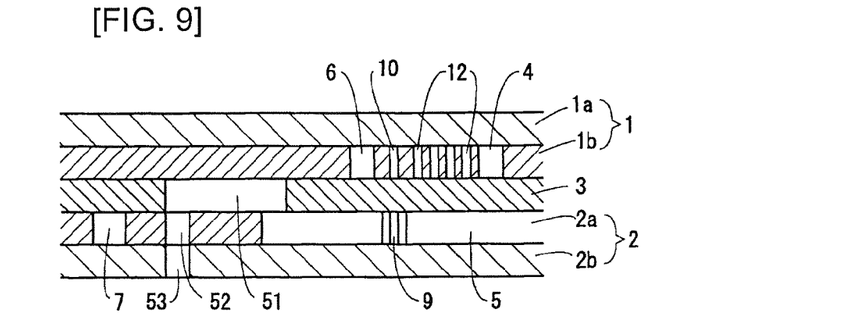
FIG. 9 is a cross-sectional view of the measuring apparatus for microanalysis taken along the line B-B shown in FIG. 2.

Next, a description is given of a measuring apparatus for microanalysis according to this embodiment with reference to FIGS. 1 to 9. FIG. 1 is a plan view showing a substrate $1a$ and FIG. 2 is a plan view showing a substrate $1b$. A first substrate 1 is formed by laying the substrates $1a$ and $1b$ one on top of another as shown in FIG. 8. FIG. 3 is an enlarged plan view showing an essential part of the substrate $1b$. FIG. 4 is a plan view showing a substrate $2a$ and FIG. 6 is a plan view showing a substrate $2b$. A second substrate 2 is formed by laying the substrates $2a$ and $2b$ one on top of another as shown in FIG. 8. FIG. 5 is an enlarged plan view showing an essential part of the substrate $2a$. FIG. 7 is a plan view showing a third substrate 3. FIG. 8 is a cross-sectional view of a measuring apparatus for microanalysis taken along the line A-A and FIG. 9 is a cross-sectional view of the measuring apparatus for microanalysis taken along the line B-B. Note that in this measuring apparatus for microanalysis, m=n=4.

As shown in FIG. 2, through holes $4_1$, $4_2$, $4_3$ and $4_4$ for first microchannels and through holes $6_1$, $6_2$, $6_3$ and $6_4$ for a third microchannel are formed in the measuring apparatus for microanalysis. The through holes $6_1$, $6_2$, $6_3$, $6_4$ for a third microchannel are formed at regular intervals and in parallel with each other. The through holes $6_1$, $6_2$, $6_3$, $6_4$ for a third microchannel are connected at their one ends to a through hole 6 for a third microchannel.

In the measuring apparatus for microanalysis, sixteen elongated through holes $10_{11}$, $10_{12}$, $10_{13}$, $10_{14}$ . . . $10_{43}$, $10_{44}$ for chambers are formed in an array of four rows and four columns at regular intervals. The through holes $10_{11}$ . . . $10_{41}$ for chambers of the first column are communicated at their upstream ends with the through hole $6_1$ for a third microchannel. The through holes $10_{12}$, . . . $10_{42}$ for chambers of the second column are communicated at their upstream ends with the through hole $6_2$ for a third microchannel. The through holes $10_{13}$, . . . $10_{43}$ for chambers of the third column are communicated at their upstream ends with the through hole $6_3$ for a third microchannel, and the through holes $10_{14}$, . . . $10_{44}$ for chambers of the fourth column are communicated at their upstream ends with the through hole $6_4$ for a third microchannel.

The through hole $4_1$ for a first microchannel is connected to through holes $8_{11}$, . . . $8_{41}$ for passive valves at regular intervals. The through hole $4_2$ for a first microchannel is connected to through holes $8_{12}$, . . . $8_{42}$ for passive valves at regular intervals. The through hole $4_3$ for a first microchannel is connected to through holes $8_{13}$, . . . $8_{43}$ for passive valves at regular intervals. The through hole $4_2$ for a first microchannel is connected to through holes $8_{14}$, . . . $8_{44}$ for passive valves at regular intervals. As shown in FIG. 3, each passive valve 8 includes a valve 81 and a weighing part 82 and the weighing part 82 is formed of a microchannel narrower than the first microchannel 4. The valve 81 is formed to be narrower than both the weighing part 82 and the chamber 10 and connected to the associated chamber 10.

The through holes $10_{11}$, $10_{12}$, $10_{13}$, $10_{14}$ . . . $10_{43}$, $10_{44}$ for chambers are connected at their respective downstream ends to through holes $12_{11}$, $12_{12}$, $12_{13}$, $12_{14}$ . . . $12_{43}$, $12_{44}$ for mixture channels, respectively, Each through hole 12 for a mixture channel constitutes a microchannel and is formed in the shape bent at right angles and turned back. In other words, each through hole 12 for a mixture channel is formed in the shape bent a plurality of times on its way and directing both ends in the same direction. The downstream end of each through hole 12 for a mixture channel is connected to a sensing part 11 that will be formed when the first substrate 1 is laid on top of the third substrate 3. Note that the reference characters $11_{11}$, $11_{12}$, $11_{13}$, $11_{14}$ . . . $11_{43}$, $11_{44}$ shown in FIG. 2 indicate the positions of the sensing parts 11 that will be formed when the first substrate 1 is laid on top of the third substrate 3 shown in FIG. 7.

The first substrate 1 formed by laying the substrate $1a$ and the substrate $1b$ one on top of another has one surface in which recesses for mixture channels 12, recesses for chambers 10, recesses for first microchannels 5, recesses for passive valves 8 communicated with the recesses for first microchannels and the recesses for chambers, and a recess for the third microchannel 6 are formed.

As shown in FIG. 4, in the substrate $2a$, through holes $5_1$, $5_2$, $5_3$ and $5_4$ for second microchannels are formed at regular intervals and in parallel with each other and through holes $7_1$, $7_2$, $7_3$ and $7_4$ for a waste solution microchannel are formed at regular intervals and in parallel with each other. The through holes $7_1$, $7_2$, $7_3$ and $7_4$ for a waste solution microchannel are connected at their one ends to a through hole 7 for a waste solution microchannel.

The through hole $5_1$ for a second microchannel is connected to through holes $9_{11}$, $9_{12}$, $9_{13}$, $9_{14}$ for passive valves. The through hole $5_2$ for a second microchannel is connected to through holes $9_{21}, \ldots 9_{24}$ for passive valves. The through hole $5_3$ for a second microchannel is connected to through holes $9_{31}, \ldots 9_{34}$ for passive valves. The through hole $5_4$ for a second microchannel is connected to through holes $9_{41}, \ldots 9_{44}$ for passive valves. As shown in FIG. 5, each passive valve 9 includes a valve 91 and a weighing part 92. The weighing part 92 is formed to be narrower than the second microchannel 5. The valve 91 is formed to be narrower than both the weighing part 92 and the chamber 10. The distal end 91a of the valve 91 shown in FIG. 5 is connected to the associated chamber 10 as shown in FIG. 3.

Referring to FIG. 7, the third substrate 3 has sixteen through holes $93_{11}, 93_{12}, 93_{13}, 93_{14} \ldots 93_{43}, 93_{44}$ for valves formed therein in an array of four rows and four columns at regular intervals. The diameter and shape of each through hole 93 for a valve are the same as those of the valve 91. When the third substrate 3 and the substrate 2a are laid one on top of another, each through hole 93 for a valve is connected to the associated valve 91. When the third substrate 3 and the substrate 1b are laid one on top of another, each through hole 93 for a valve is connected to the associated chamber 10.

As shown in FIG. 5, the through holes $7_1, 7_2, 7_3$ and $7_4$ for a waste solution microchannel are connected to sixteen extended through holes 71 in total, with each through hole for a waste solution microchannel connected to four extended through holes 71. The through holes $7_1, 7_2, 7_3, 7_4$ for a waste solution microchannel are formed in communication with the sensing parts 11.

Referring back to FIG. 7, the third substrate 3 also has sixteen through holes $11_{11}, 11_{12}, 11_{13}, 11_{14} \ldots 11_{43}, 11_{44}$ for sensing parts formed therein in an array of four rows and four columns at regular intervals. The through holes $11_{11}, 11_{12}, 11_{13}, 11_{14}$ for sensing parts are formed so that when the third substrate and the substrate 2a are laid one on top of another, the extended through holes 71 of the through hole $7_1$ for a waste solution microchannel are connected to the respective associated through holes $11_{11}, 11_{12}, 11_{13}, 11_{14}$ for sensing parts, the extended through holes 71 of the through hole $7_2$ for a waste solution microchannel are connected to the respective associated through holes $11_{21}, \ldots 11_{24}$ for sensing parts, the extended through holes 71 of the through hole $7_3$ for a waste solution microchannel are connected to the respective associated through holes $11_{31}, \ldots 11_{34}$ for sensing parts, and the extended through holes 71 of the through hole $7_4$ for a waste solution microchannel are connected to the respective associated through holes $11_{41}, 11_{42}, 11_{43}, 11_{44}$ for sensing parts.

When the substrate 2a and the substrate 2b are laid one on top of another, the second substrate 2 is formed that has one surface in which recesses for second microchannels, recesses for passive valves 9 connected to the recesses for second microchannels, and a recess for a waste solution microchannel 7 are formed.

In the substrates 2a, 2b and the third substrate 3, through holes $41_1$ to $41_4$, $42_1$ to $42_4$, $43_1$ to $43_4$, $44_1$ to $44_4$, $45_1$ to $45_4$ and $46_1$ to $46_4$ are formed. Out of the through holes $41_1$ to $41_4$, $42_1$ to $42_4$, $43_1$ to $43_4$, $44_1$ to $44_4$, $45_1$ to $45_4$ and $46_1$ to $46_4$, the through holes $41_1, 42_1$ and $43_1$ are formed so that when the substrate 1b, the third substrate 3, the substrate 2a and the substrate 2b are laid one on top of another in this order, this set of through holes are connected to one end of the through hole $4_1$ for a first microchannel. Likewise, the through holes $41_2$ to $41_4$, $42_2$ to $42_4$, $43_2$ to $43_4$ are formed to be connected to one ends of the through holes $4_2$ to $4_4$ for first microchannels (upper ends thereof in FIG. 2). Likewise, the through holes $44_1$ to $44_4$, $45_1$ to $45_4$, $46_1$ to $46_4$ are formed to be connected to the other ends of the through holes $4_1$ to $4_4$ for first microchannels. Therefore, when a solution is supplied through each through hole 43, the solution passes through the associated through holes 42 and 41, the first microchannel 4 and the associated through holes 44 and 45 in this order and is then exhausted through the associated through hole 46.

In the substrates 2a, 2b and the third substrate 3, through holes $51_1$ to $51_4$, $52_1$ to $52_4$, $53_1$ to $53_4$, $54_1$ to $54_4$, $55_1$ to $55_4$ and $56_1$ to $56_4$ are further formed. Out of the through holes $51_1$ to $51_4$, $52_1$ to $52_4$, $53_1$ to $53_4$, $54_1$ to $54_4$, $55_1$ to $55_4$ and $56_1$ to $56_4$, the through holes $51_1, 52_1$ and $53_1$ are formed so that when the substrate 1b, the third substrate 3, the substrate 2a and the substrate 2b are laid one on top of another in this order, this set of through holes are connected to one end of the through hole 51 for a second microchannel. Likewise, the through holes $51_2$ to $51_4$, $52_2$ to $52_4$, $53_2$ to $53_4$ are formed to be connected to one ends of the through holes $5_2$ to $5_4$ for second microchannels. Likewise, the through holes $54_1$ to $54_4$, $55_1$ to $55_4$, $56_1$ to $56_4$ are formed to be connected to the other ends of the through holes $5_1$ to $5_4$ for second microchannels. Therefore, when a solution is supplied through each through hole 53, the solution passes through the associated through holes 42 and 41, the second microchannel 5 and the associated through holes 54 and 55 in this order and is then exhausted through the associated through hole 56.

In the third substrate 3 and the substrates 2a and 2b, through holes 61, 62 and 63 are further formed. The through holes 61, 62 and 63 are formed so that when the substrate 1b, the third substrate 3 and the substrates 2a and 2b are laid one on top of another in this order, these through holes are connected to one end of the through hole 6 for a third microchannel. Therefore, a waste solution and gas exhausted from the third microchannel 6 is drained through the through holes 61 and 62 from the through hole 63.

The sensing parts 11, the chambers 10, the passive valves 8 and 9, the first microchannels 4, the second microchannels 5, the third microchannel 6 and the waste solution microchannel 7 are defined by the first substrate 1, the second substrate 2 and the third substrate 3. The inlet ports through which solution is taken into the first microchannels 4, the second microchannels 5 and the third microchannel 6 and the outlet ports through which the solution is exhausted from the first microchannels 4, the second microchannels 5, the third microchannel 6 and the waste solution microchannel 7 are all open at the second substrate 2, specifically at the substrate 2b.

The measuring apparatus for microanalysis according to this embodiment makes a measurement, such as by optical measuring methods or electrochemical analysis. Therefore, at least one of the substrates lying over and under the sensing parts is preferably transparent. Particularly, when a measurement is made with a standard equivalent to the analyte being immobilized to surface portions of the first substrate 1 facing the sensing parts, at least parts of the second substrate 2 facing the sensing parts are preferably transparent.

Examples of a material for the substrates include polydimethylsiloxane (PDMS), glass, silicon, photoreactive resin, other types of resins, metal, ceramic, diamond-like carbon, and a combination of them.

Examples of a substrate fabrication method include machining, transfer techniques as typified by injection molding and compression molding, dry etching (RIE, IE, IBE, plasma etching, laser etching, reactive ion etching, laser ablation, blasting, electric exhaust machining, LIGA, electron beam etching, FAB), wet etching (chemical etching), casting including stereolithography and layer manufacturing using beds of powdered ceramics, surface micro-machining of coating, vapor-depositing, sputtering or depositing various substances in the form of a layer and partly removing it to form a microstructure, a method of forming grooves by defining openings by one or more sheet materials made such as of a film tape, and a method of forming grooves by dropping or injecting a channel formation material by ink jet or a dispenser.

Examples of a method for bonding the substrates to each other include adhesion with an adhesive, resin bonding with a primer, diffusion bonding, anode bonding, eutectic bonding, heat fusion bonding, ultrasonic bonding, laser fusing, bonding with a solvent or a dissolved solvent, bonding with a pressure sensitive tape, boding with an adhesive tape, bonding by crosslinking of functional groups in the surface, compression bonding, bonding with a self-absorbent, physical clamping and assembly by doweling.

Although this embodiment describes a measuring apparatus for microanalysis in which five substrates are bonded together, the measuring apparatus for microanalysis may be formed of three substrates, a first substrate, a second substrate and a third substrate, wherein the substrate 1a and the substrate 1b are laminated to form an integral first substrate and the substrate 2a and the substrate 2b are laminated to form an integral second substrate.

The configuration of the measuring apparatus for microanalysis according to this embodiment is as described above. As seen from the above, the measuring apparatus for microanalysis according to this embodiment can be easily manufactured, can reduce the dead volume for sample and reagent and can provide space saving of the entire apparatus and cost reduction.

Furthermore, the measuring apparatus for microanalysis according to this embodiment includes a plurality of sensing parts 11, passive valves 8 and 9 and chambers 10, with one passive valve 8, one passive valve 9 and one chamber 10 being exclusive to each sensing part 11. Therefore, the measurements at all the sensing parts 11 can be made substantially simultaneously. If the passive valves 8 and the passive valves 9 are configured to weigh out different amounts of 1 solution, different kinds of mixed solutions having different mixing ratios between the sample and the reagent for detecting the analyte can be introduced into a plurality of sensing parts 11. Therefore, for a single kind of sample, a plurality of kinds of mixed solutions having different mixing ratios between the sample and the reagent for detecting the analyte can be measured simultaneously by using a single measuring apparatus for microanalysis.

Furthermore, if the passive valves are configured to weigh out equal amounts of solution, the kinds of sample and reagent fed to the plurality of sensing parts 11 can be changed from column to column or from row to row. Therefore, different kinds of samples can be simultaneously measured by using a single measuring apparatus for microanalysis and a plurality of analytes for a single kind of sample using different kinds of reagents can be simultaneously measured by using a single measuring apparatus for microanalysis.

As described so far, according to the measuring apparatus for microanalysis of this embodiment, a plurality kinds of measurements can be made simultaneously. Specifically, according to this embodiment, since sixteen sensing parts 11 are provided in total, sixteen kinds of measurements at most can be made simultaneously by using a single measuring apparatus for microanalysis.

Next, a description is given of a microanalysis measuring method using the measuring apparatus for microanalysis according to this embodiment. First, a standard equivalent to the analyte is immobilized to surface portions of the first substrate 1 facing the sensing parts 11. Next, a sample containing an analyte is fed to the first microchannels 4 and then weighed out in the passive valves 8. On the other hand, a reagent containing recognition molecules bindable specifically to the analyte is fed to the second microchannels 5 and then weighed out in the passive valves 9.

A fixed amount of sample containing the analyte and weighed out in each passive valve 8 is pressurized such as by supplying gas from a gas supply source to the associated first microchannel 4 and thereby fed through the weighing part 82 and the valve 81 to the associated chamber 10. A fixed amount of reagent containing the recognition molecules bindable specifically to the analyte and weighed out in each passive valve 9 is pressurized such as by supplying gas from a gas supply source to the associated second microchannel 5 and thereby fed through the weighing part 92, the valve 91 and the through hole 93 for the valve to the associated chamber 10. In each chamber 10, the sample containing the analyte and the reagent containing the recognition molecules bindable specifically to the analyte are mixed, thereby preparing a mixed solution.

The mixed solution in the chamber 10 is pressurized by supplying gas from a gas supply source to the third microchannel 6 and thereby fed through the associated mixture channel 12 to the associated sensing part 11. The mixed solution is further uniformly mixed in the mixture channel 12, whereby the analyte in the mixed solution reacts to the recognition molecules bindable specifically to the analyte. In each sensing part 11, unreacted recognition molecules in the mixed solution bind to the standard that is immobilized to a surface portion 11a of the first substrate in the sensing part 11 and is equivalent to the analyte. Thereafter, the sensing part 11 is washed and the recognition molecules bound to the standard immobilized to the surface portion 11a of the first substrate are optically measured by optical labels providing fluorescence, light scattering or light absorption.

Second Embodiment

The first embodiment describes the microanalysis measuring method using a reagent containing recognition molecules bindable specifically to the analyte. However, instead of the reagent containing recognition molecules bindable specifically to the analyte, a reagent producing a color or emitting light by reaction specific to the analyte may be used. In such a case, the sensing parts 11 detect the production of color of the reagent or the emission of light of the reagent.

Third Embodiment

Instead of the reagent containing recognition molecules bindable specifically to the analyte in the first embodiment, a reagent containing a substance forming aggregates by reaction specific to the analyte may be used. In this case, turbidity of the mixed solution is detected at the sensing part 11.

Fourth Embodiment

Figure 13:
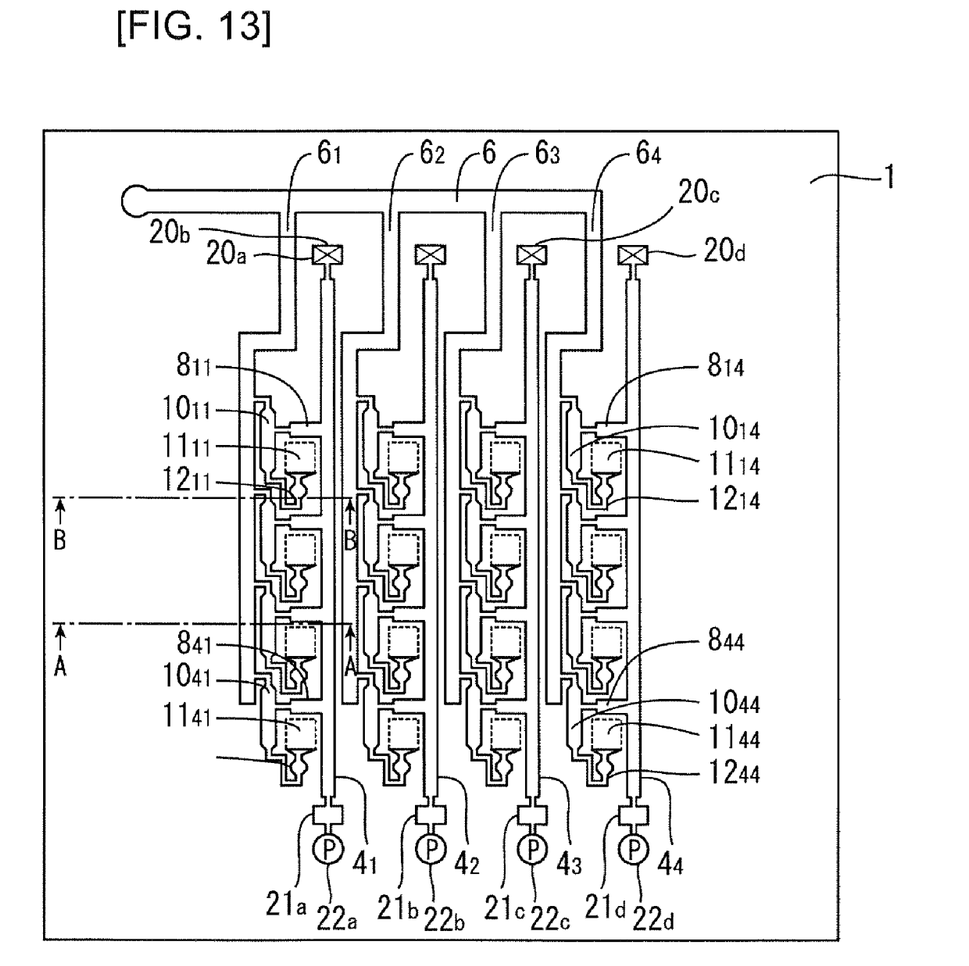
FIG. 13 is a plan view of a substrate 1a of a measuring apparatus for microanalysis according to a fourth embodiment.

FIG. 13 is a plan view of a substrate 1a of a measuring apparatus for microanalysis according to a fourth embodiment. The measuring apparatus for microanalysis according to the fourth embodiment is different from that according to the first embodiment in that it includes stop valves 20a, 20b, 20c, 20d, reagent reservoirs 21a, 21b, 21c, 21d and pumps 22a, 22b, 22c, 22d serving as gas supply sources. Specifically, in this embodiment, the through holes $4_1, 4_2, 4_3$ and $4_4$ for first microchannels are provided, at their downstream ends located at their upper ends in FIG. 13, with stop valves 20a, 20b, 20c and 20d, respectively. On the other hand, the upstream ends of the through holes $4_1, 4_2, 4_3$ and $4_4$, located at the lower ends thereof in FIG. 13, are connected through reagent reservoirs 21a, 21b, 21c and 21d to pumps 22a, 22b, 22c and 22d, respectively.

Thus, by previously storing in the reagent reservoirs 21a, 21b, 21c and 21d solution to be weighed out in the passive valves 8, the solution can be easily fed to the passive valves 8 by activating the pumps 22a, 22b, 22c and 22d. Furthermore, the provision of the stop valves 20a, 20b, 20c and 20d enables solution left in the through holes $4_1$, $4_2$, $4_3$ and $4_4$ for first microchannels without being fed to the passive valves 8 to be easily removed from the connection parts of the through holes $4_1$, $4_2$, $4_3$ and $4_4$ for first microchannels connected with the passive valves 8. Therefore, according to the measuring apparatus for microanalysis of the fourth embodiment, solution can be easily weighed out in the passive valves 8.

Without the provision of stop valves 20a, 20b, 20c and 20d, the downstream ends of the through holes $4_1$, $4_2$, $4_3$ and $4_4$ for first microchannels must have complicated structures in order to remove residual solution in the through holes $4_1$, $4_2$, $4_3$ and $4_4$ for first microchannels from the parts thereof connected with the passive valves 8. Therefore, the downstream ends of the through holes $4_1$, $4_2$, $4_3$ and $4_4$ for first microchannels will generally have complicated structures. In contrast, the provision of stop valves 20a, 20b, 20c and 20d as in this embodiment eliminates the need for complicated structures of the downstream ends of the through holes $4_1$, $4_2$, $4_3$ and $4_4$ for first microchannels, which would otherwise been needed, and can prevent the downstream ends of the through holes $4_1$, $4_2$, $4_3$ and $4_4$ for first microchannels from being complicated. In short, the structure of the measuring apparatus for microanalysis can be simplified by providing of the stop valves 20a, 20b, 20c and 20d.

In view of easy weighing-out of solution in each passive valve 9, it is preferable that stop valves, reagent reservoirs and pumps are provided likewise also on the side of the passive valves 9.

This embodiment describes a structure in which the pumps 22a, 22b, 22c and 22d are disposed within the measuring apparatus for microanalysis. However, the pumps 22a, 22b, 22c and 22d may be disposed outside of the measuring apparatus for microanalysis.

The invention claimed is:

1. A measuring apparatus for microanalysis comprising: sensing parts in an array of m rows and n columns, each of the sensing parts being communicated with a waste solution microchannel; chambers in an array of m rows and n columns, the chambers being communicated through respective mixture channels to the respective sensing parts, n first microchannels each communicated through m passive valves with the respective m chambers, one chamber per each row of chambers; m second microchannels each communicated through n passive valves with the respective n chambers, one chamber per each column of chambers; and a third microchannel, communicated with the chambers, for supplying gas and/or washing solution to the chambers, wherein the first microchannels, the second microchannels and the third microchannel are connected to respective gas supply sources.

2. The measuring apparatus for microanalysis of claim 1, wherein the n first microchannels are separated from each other.

3. The measuring apparatus for microanalysis of claim 1, wherein the m second microchannels are separated from each other.

4. The measuring apparatus for microanalysis of claim 1, wherein the volume of each chamber and the volume of each sensing part are of the order of picoliters to microliters and the volume of the chamber is equal to or larger than the volume of the sensing part.

5. The measuring apparatus for microanalysis of claim 1, wherein recesses for the mixture channels, recesses for the chambers, recesses for the first microchannels, recesses for the passive valves each communicated with one of the recesses for the first microchannels and one of the recesses for the chambers and a recess for the third microchannel are formed in one surface of a first substrate, recesses for the second microchannels, recesses for the passive valves each communicated with one of the recesses for the second microchannels and a recess for the waste solution microchannel are formed in one surface of a second substrate, through holes for the sensing parts and through holes communicating the respective recesses for the chambers with the respective passive valves communicated with the second microchannels are formed in a third substrate, and the sensing parts, the chambers, the passive valves, the first microchannels, the second microchannels, the third microchannel and the waste solution microchannel are formed by laying the third substrate between the one surface of the first substrate and the one surface of the second substrate.

6. The measuring apparatus for microanalysis of claim 5, wherein the second substrate or parts of the second substrate facing the sensing parts are transparent.

7. The measuring apparatus for microanalysis of claim 5, wherein a standard equivalent to an analyte is immobilized on surface portions of the first substrate facing the sensing parts.

8. A microanalysis measuring method comprising: feeding a sample containing an analyte and a reagent containing recognition molecules bindable specifically to the analyte to each of the first microchannels and each of the second microchannels, respectively, in the measuring apparatus for microanalysis of claim I; weighing out the analyte and the reagent in the associated passive valves; feeding each pair of analyte and reagent thus weighed out to the associated chamber into a mixed solution, causing mixing and reaction of the mixed solution in the chamber and the associated mixture channel; then feeding the mixed solution to the associated sensing part to bind unreacted recognition molecules in the mixed solution to a standard immobilized to the sensing part; cleaning the sensing part; and then optically measuring the recognition molecules bound to the standard with optical labels providing fluorescence, light scattering or light absorption.

9. A microanalysis measuring method comprising: feeding a sample containing an analyte and a reagent containing recognition molecules bindable specifically to the analyte to each of the first microchannels and each of the second microchannels, respectively, in the measuring apparatus for microanalysis of claim 1; weighing out the analyte and the reagent in the associated passive valves; feeding each pair of analyte and reagent thus weighed out to the associated chamber into a mixed solution, causing mixing and reaction of the mixed solution in the chamber and the associated mixture channel; then feeding the mixed solution to the associated sensing part to bind unreacted recognition molecules in the mixed solution to a standard immobilized to the sensing part; washing the sensing part; and then electrochemically measuring the recognition molecules bound to the standard.

10. A microanalysis measuring method comprising: feeding a sample containing an analyte and a reagent producing a color or emitting light by reaction specific to the analyte to each of the first microchannels and each of the second microchannels, respectively, in the measuring apparatus for microanalysis of claim 1; weighing out the analyte and the reagent in the associated passive valves; feeding each pair of analyte and reagent thus weighed out to the associated chamber into a mixed solution, causing mixing and reaction of the mixed solution in the chamber and the associated mixture channel; and measuring the produced color or the emitted light of the mixed solution in the associated sensing part.

11. A microanalysis measuring method comprising: feeding a sample containing an analyte and a reagent forming aggregates by reaction specific to the analyte to each of the first microchannels and each of the second microchannels, respectively, in the measuring apparatus for microanalysis of claim 1; weighing out the analyte and the reagent in the associated passive valves; feeding each pair of analyte and reagent thus weighed out to the associated chamber into a mixed solution, causing mixing and reaction of the mixed solution in the chamber and the associated mixture channel; and measuring the turbidity of the mixed solution in the associated sensing part.

12. A microanalysis measuring method comprising: feeding a sample containing an analyte and a reagent containing recognition molecules bindable specifically to the analyte to each of the first microchannels and each of the second microchannels, respectively, in the measuring apparatus for microanalysis of claim 1; weighing out the analyte and the reagent in the associated passive valves; feeding each pair of analyte and reagent thus weighed out to the associated chamber into a mixed solution, joining each of analyte recognition molecules of another kind immobilized in the chamber, the analyte and the recognition molecule derived from the reagent in a sandwiched method; then introducing through the third microchannel into the chamber a solution of a substance digestable with a labeling enzyme on the recognition molecule to displace the mixed solution in the chamber; introducing a product obtained by digestion with the labeling enzyme to the associated sensing part and trapping the product in the sensing part; and indirectly determining the analyte concentration in the sample by measuring the concentration of the product in the sensing part.

13. The measuring apparatus for microanalysis of claim 1, wherein the measuring apparatus further comprises the gas supply sources.

14. The measuring apparatus for microanalysis of claim 5, wherein the measuring apparatus further comprises a through hole connecting one end of the first microchannel and an aperture of the measuring apparatus and a through hole connecting one end of the second microchannel and an aperture of the measuring apparatus.

* * * * *